United States Patent [19]
Zajer nee Balazs et al.

[11] 4,328,231
[45] May 4, 1982

[54] METHOD OF TREATING PSORIASIS

[75] Inventors: Mária Zájer née Balázs; Lilla Forgách; Egon Kárpáti; Árpád Király; Gyöngyvér Király née Soos; László Szporny; Béla Rosdy, all of Budapest, Hungary

[73] Assignee: Richter Gedeon Vegyeszeti Gyar Rt., Budapest, Hungary

[21] Appl. No.: 172,169

[22] Filed: Jul. 25, 1980

[30] Foreign Application Priority Data

Aug. 16, 1979 [HU] Hungary .................. RI 724

[51] Int. Cl.³ .......................................... A61K 31/435
[52] U.S. Cl. ................................................... 424/256
[58] Field of Search ........................................ 424/256

[56] References Cited

U.S. PATENT DOCUMENTS 4,065,458 12/1977 Lorincz et al. ................. 260/293.55

OTHER PUBLICATIONS

Chemical Abstracts 76:34460j; 34461k, (1972).
The Merck Manual, 10th ed., pp. 1472–1474, (1961).

Primary Examiner—Leonard Schenkman
Attorney, Agent, or Firm—Karl F. Ross

[57] ABSTRACT

Skin diseases such as psoriasis in a human patient can be treated by topically or parenterally administering a dermatological composition containing a compound of the formula:

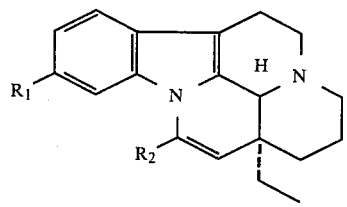

wherein
$R_1$ is hydrogen and
$R_2$ is the group —COOCH$_3$, —CONH$_2$, or —CONHNH$_2$; or
$R_1$ is methoxy and
$R_2$ is a group

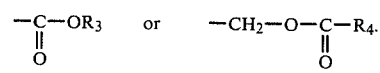

4 Claims, No Drawings

METHOD OF TREATING PSORIASIS

The present invention relates to dermatological compositions for treating skin diseases which are accompanied by pathological cell proliferation. More particularly, this invention concerns new dermatological compositions containing a compound of the formula (I)

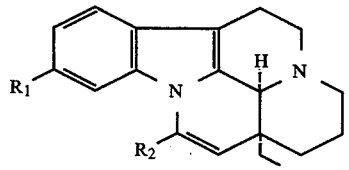

or a pharmaceutically acceptable salt thereof as active ingredient.

The formula (I) encompasses apovincaminic acid derivatives and apovincine and derivatives thereof.

In the case of apovincaminic acid derivatives, in the formula (I)
$R_1$ is hydrogen and
$R_2$ is the group $-COOCH_3$, $-CO-NH_2$ or $-CO-NH-NH_2$;
in the case of apovincine and derivatives thereof
$R_1$ is methoxy and
$R_2$ is a group

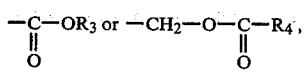

wherein
$R_3$ represents an alkyl group having 1 to 5 carbon atoms,
$R_4$ represents an alkyl group having 1 to 4 carbon atoms or a trimethoxyphenyl group.

The compounds of the formula (I) are known in the art. Apovincamine ($R_1$=hydrogen and $R_2$=—COOCH$_3$) was described by Trojanek et al. [Tetrahedron Letters 20, 702–706, (1961), Pergamon Press Ltd.] and apovincaminic acid hydrazide and amide ($R_1$=hydrogen and $R_2$=carboxylic acid amide or acid hydrazide) are disclosed in the British Pat. No. 1,252,618.

Apovincine was also described by Trojanek [Coll. Czechoslov. Chem. Commun 29, 447 (1964)] ($R_1$=methoxy, $R_2$=—COOCH$_3$), while apovincinic acid ethyl ester ($R_1$=methoxy and $R_2$=—COOC$_2$H$_5$) is disclosed in the Belgian Pat. No. 869,274, and finally the esters of apovincinol ($R_1$=methoxy,

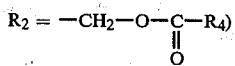

are reported in the U.S. Pat. No. 4,065,458.

According to the above-listed publications the compounds show vasotropic activity. Also the publications relating to the alkaloids of Vinca minor L. and their known derivatives disclose generally vasotropic activity, and up to the present time nothing has been published in connection with compounds having an eburnane skeleton which would suggest their dermatological utilization or the possibility of any kind of topical treatment.

It is therefore highly surprising and cannot be derived from the earlier results that the compounds of the formula (I) and pharmaceutically acceptable salts thereof are capable of treating skin diseases accompanied by pathological cell proliferation.

Diseases accompanied by a pathological epidermal cell proliferation are relatively frequent and concern several percent of the population. They include diseases such as proriasis atopic dermatitis, primary contact dermatitis, allergic contact dermatitis, ichthyosis, sun-induced keratosis, acne and seborrheic dermatitis. Some of the above listed diseases are typical for human, while others appear also on animals.

Since some of the skin diseases accompanied by pathological cell proliferation e.g. psoriasis, cannot be induced on animals, the antipsoriatic activity of apovincaminic acid ethyl ester and pharmaceutically acceptable salts thereof can only indirectly be rendered probable via animal tests.

Voorhees et al. [Arch. Derm. 104, 359–365 (1961)] have observed that parallel with a pathological cell proliferation the level of cyclic adenosine monophosphate (c-AMP) is decreased. As it is well known, c-AMP is produced by the enzyme adenyl cyclase and is deactivated by phospho-diesterase. Voorhees succeeded in influencing psoriasis with agents which stimulate the function of adenyl cyclase (for example norepinephrine) or inhibit the function of phosphodiesterase (such as theophylline, papaverine).

Our working hypothesis was based on the assumption that if it can be proved that a certain compound inhibits the function of phosphodiesterase, we have a good reason to believe that said compound is capable of treating psoriasis or other skin diseases which are accompanied by pathological cell proliferation.

Our model experiments were carried out by means of phosphodiesterase isolated from animal tissues. More particularly, the enzyme was isolated from the brain tissue of rats following the method of J. Schröder and H. V. Richenberg [Biochem. Biophys. Acta 302, 50 (1973)], whereupon the isolated phosphodiesterase was purified by the method of J. G. Hardman and E. W. Sutherland [J. Biol. Chem. 240, 3704 (1965)]. Finally, the activity of the purified enzyme was measured by the radioisotopic technique of G. Pöch, in the presence of an excess amount of tritium-labelled c-AMP, in an incubator, initially without the inhibiting system and thereafter in the presence of a compound of the formula (I) as an inhibitor. The enzyme activity was determined after an incubation time of 20 minutes [N. S. Arch. Pharmacol. 268, 272 (1971)]. From the salts of the test compounds of the formula (I) aqueous $10^{-3}$ molar stock solutions were prepared, their pH was adjusted to 4 to 5. To the incubated enzyme preparations suitable amounts of the stock solution were added in order to obtain a series of test solutions containing a compound of the formula (I) in a concentration of $10^{-5}$, $5 \times 10^{-5}$, $10^{-4}$, $5 \times 10^{-4}$ and $10^{-3}$ moles/lit. The enzyme activity of the reference compounds, such as papaverine, diaphylline, theophylline and prednisolone homosuccinate was determined in an analogous way. The degree of inhibition (decrease of enzyme activity) was expressed in % of the control (enzyme preparation containing no inhibitor).

The results obtained are summarized in the following Table:

| Compound of the formula (I) or reference compound | Inhibition (%) obtained by | | | | |
|---|---|---|---|---|---|
| | $5 \times 10^{-6}$ | $1 \times 10^{-5}$ | $5 \times 10^{-5}$ | $1 \times 10^{-4}$ | $1 \times 10^{-3}$ |
| | moles/lit. concentrations of the test compounds | | | | |
| Apovincamine | 21.9 | 20.3 | 33.5 | 54.8 | |
| Apovincaminic acid amide | 10.0 | 22.0 | 60.0 | 76.9 | |
| Apovincaminic acid-hydrazide | | | 32.0 | 57.0 | |
| Apovincine-KHSO$_4$ | 36.6 | 49.0 | 59.4 | 71.8 | |
| Apovincine-tartrate | 38.1 | 48.7 | 76.9 | 81.6 | |
| Apovincinic acid ethyl ester tartrate | | 23.7 | 44.0 | 58.6 | |
| Tartrate salt of apo-vincinol-acetate | 30.9 | 34.8 | 45.2 | 62.3 | |
| Tartrate salt of apo-vincinol-propionate | 15.0 | 23.8 | 57.8 | 75.0 | |
| Salt of Apovincinol-3',4',5'-trimethoxy-benzoate | 55.9 | 70.0 | 71.5 | 81.5 | |
| Papaverine | | | 36.4 | 56.4 | |
| Diaphylline | | | 3.0 | 25.0 | 55.7 |
| Theophylline | | | | 23.0 | 58.0 |
| Prednisolone-hemi-succinate | | 9.2 | 21.3 | 42.4 | |

From the above data it can be clearly seen that most of the compounds of the formula (I) tested have a better inhibitory effect than the reference substances.

The most effective compound, apovincinol-3',4',5'-trimethoxy-benzoate is about 500-times more effective than diaphylline and is about 50-times more effective than the best reference compound, papaverine.

The first clinical tests have been carried out by compositions suitable for topical treatment, such as ointments, creams, solutions, tinctures, pastes, aerosol preparations, containing the compounds which proved the best in the in vitro tests, as active ingredient. More particularly, creams containing 2%, 1%, 0.5%, 0.25% and 0.1%, respectively of apovincine and creams containing 3',4',5'-trimethoxy benzoate in the above concentrations have been employed.

For clinical study, psoriasis patients were selected who have not received any systemic, such as immunosupressive, cytostatic or glucocorticoid, treatment.

The test groups consisted of 5 patients, and the selected lesions on such patients were studied by the so-called plaques method. One side of the symmetrically located lesions were tested with an active ingredient-containing cream, while the other side was treated with a placebo. The remaining skin surface was treated by traditional topical methods, for example with ointments containing flumethasone pivalate and salicylic acid as active ingredient.

The treatment was started with the more concentrated creams, and further patients have been treated with creams containing the minimum effective amount of the active compound. The cream was applied to the skin 2 to 3 times a day until the symptoms were eliminated or improved (about 1 to 6 weeks).

The evaluation of the clinical tests involved three symptoms, namely inflammation, infiltration and peeling. The intensity of the individual symptoms was rated between 0 and 3 and the effect was characterized by the sum of the scores obtained on the three different symptoms. The results were worked up by methods of the mathematical statistics.

The results unambiguously showed that the compositions according to the invention can successfully be used for curing psoriasis and show no side effects.

The invention relates to dermatological compositions inhibiting phosphodiesterase activity, first of all for preventing the re-occurance and curing skin diseases accompanied by pathological cell proliferation which comprise a compound of the formula (I)

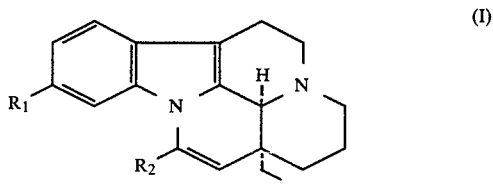

wherein
R$_1$ is hydrogen and
R$_2$ is the group —COOCH$_3$, —CO—NH$_2$ or —CO—NH—NH$_2$; or
R$_1$ is methoxy and
R$_2$ is a group

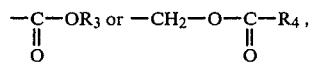

wherein
R$_3$ is alkyl having 1 to 5 carbon atoms and
R$_4$ is alkyl having 1 to 4 carbon atoms or a trimethoxyphenyl group
or a pharmaceutically acceptable salt thereof and optionally one or more further pharmaceutically active compound(s) in admixture with at least one pharmaceutically inert carrier or diluent.

According to another aspect of the invention there is provided a method for the preparation of said compositions, which comprises mixing a compound of the formula (I) wherein R$_1$, R$_2$, R$_3$ and R$_4$ are as defined above, or a pharmaceutically acceptable salt thereof and optionally at least one further pharmaceutically active compound with at least one pharmaceutically inert carrier or diluent.

The compositions according to the invention contain 0.1 to 8.0%, preferably 0.2 to 2.0% of active ingredient. The further pharmaceutically active compounds can for example be antibiotics, cytostatics, prostaglandins, ditranole, salicyclic acid, tar, anti-inflammatory or immunosupressive agents, glucocorticoids and, in the case of parenteral administration, local anaesthetics.

According to a preferred embodiment of the invention compositions suitable for topical application, such as creams, ointments, solutions, gelées, aerosols, aerosol foams, plasters, etc. are prepared.

The active ingredient is preferably used as a free base, but pharmaceutically acceptable salts thereof, for example its tartrate or alkali metal hydrogensulfate, etc. can also be employed.

The active ingredient is preferably incorporated into a cream, which can be washed down.

For the preparation of creams the active substance is dissolved in an alcoholic solvent, preferably in propylene or dipropylene glycol, or in a mixture thereof with a small amount of water, and the solution obtained is admixed with a well smearable skin-compatible fatty phase.

The fatty phase can contain cetyl, stearyl or cetostearyl alcohol, paraffin oil, glycerine monostearate, etc.

The cream can further contain emulsifyers, preferably polyoxyethylene sorbitane monooleate or monostearate, and preservatives, such as benzoic acid derivatives, preferably p-hydroxybenzoic acid methyl ester.

The creams preferably contain 0.25 to 2.0% of active ingredient, 45 to 50% of glycol, 23 to 27% of paraffine oil, 11 to 15% of stearyl alcohol and other additives ad 100%.

The active ingredients can be formulated also as ointments which cannot be washed down with water. In this case the active ingredient is directly incorporated into the fatty phase.

Solutions can also be prepared, which contain for example 20 to 40% of propylene glycol or dipropylene glycol, 40 to 55% of a 96% ethanol and distilled water ad 100% as a solvent.

If the pharmaceutical compositions are formulated as aerosol preparations, to a solution of the active ingredient in propylene glycol a fat, preferably isopropyl myristate and a propellant, preferably a freon are added.

Aerosol foams can for example be prepared by adding an alcoholic solution of the active ingredient to a mixture of 0.5 to 1.5% of cetostearyl alcohol, 1 to 3% of benzyl alcohol, 15 to 20% of polyoxyethylene sorbitane monooleate or -monostearate and 25 to 30% of water, whereupon as a propellant, freon is added.

For parenteral administration, preferably for subcutaneous or intracutaneous application injection solutions can be prepared. For this purpose a salt of the active ingredient is dissolved for example in a 0.72% aqueous sodium chloride solution, and the pH of the solution is adjusted to 5.

Further details of our invention are illustrated in the following Examples but it is not intended to limit the scope of the invention to the Examples.

EXAMPLE 1

Preparation of creams

| Apovincanol-3',4',5'-trimethoxy benzoate | 2 g. |
| --- | --- |
| Propylene glycol | 50 g. |
| Paraffin oil | 26 g. |
| Polyethylene glycol 400 | 5 g. |
| Stearyl alcohol | 15 g. |
| Glycerine monostearate | 2 g. |

The active ingredient is dissolved in propylene glycol on a water bath the temperature of which does not exceed 50° C. The remaining components are heated up to the melt, whereupon are cooled to 40° to 45° C. Thereafter the solution of the active ingredient is added to the melt with stirring, and the cream obtained is cooled under continuous stirring.

Creams containing 0.25, 0.5, 1.0 and 1.5% of the active ingredient can be prepared in an analogous way.

EXAMPLE 2

Preparation of creams

The procedure described in Example 1 is followed except that 0.5 to 2% of apovincine is employed as active ingredient.

EXAMPLE 3

Preparation of creams

The procedure described in Example 1 is followed except that 0.5 to 2% apovincamine or apovincaminic acid amide is used as active ingredient.

EXAMPLE 4

Preparation of creams containing two active ingredients

| Apovincinol-3',4',5'-trimethoxy benzoate | 2.0 g. |
| --- | --- |
| Triamcinolone acetonide | 0.1 g. |
| Glycerine monostearate | 3.0 g. |
| Polyethylene glycol 400 | 5.0 g. |
| Stearyl alcohol | 13.0 g. |
| Paraffin oil | 24.9 g. |
| Propylene glycol | 53.0 g. |

The procedure described in Example 1 is followed except that two active ingredients are dissolved in propylene glycol.

EXAMPLE 5

Preparation of a solution

| Apovincinol-3',4',5'-trimethoxy benzoate | 1% |
| --- | --- |
| Propylene glycol | 30% |
| 96% ethanol | 47% |
| Distilled water | 22% |

A solution is prepared from the above listed ingredients.

EXAMPLE 6

Preparation of an aerosol

| Apovincinol-3',4',5'-trimethoxy benzoate | 0.5% |
| --- | --- |
| Propylene glycol | 30.0% |
| Isopropyl myristate | 4.5% |
| Freon | 65.0% |

An aerosol formulation is prepared by conventional techniques using the above ingredients.

EXAMPLE 7

Preparation of an aerosol foam

| | |
|---|---|
| Apovincinol-3',4',5'-trimethoxy benzoate | 2% |
| Cetostearyl alcohol | 1% |
| Benzyl alcohol | 2% |
| Polyoxyethylene sorbitane monostearate | 15% |
| 96% ethanol | 30% |
| Distilled water | 30% |
| Freon | 20% |

An aerosol foam is prepared by conventional techniques using the above ingredients.

We claim:

1. A method of treating psoriasis in a human patient which comprises the step of topically or parenterally administering a dermatological composition, containing a dermatologically effective amount of a compound of the formula I

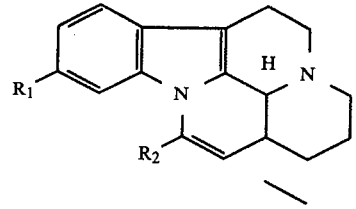

wherein
$R_1$ is hydrogen and
$R_2$ is the group —COOCH$_3$, —CONH$_2$, or —CONHNH$_2$; or
$R_1$ is methoxy and
$R_2$ is a group

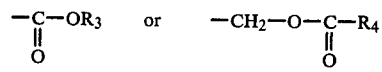

wherein $R_3$ is alkyl having 1 to 5 carbon atoms and $R_4$ is alkyl having 1 to 4 carbon atoms or trimethoxyphenyl, or a pharmaceutically acceptable salt thereof in admixture with a pharmaceutically acceptable inert carrier.

2. The method defined in claim 1 wherein the compound of the formula I is apovincinol-3',4',5'-trimethoxybenzoate or a pharmaceutically acceptable salt thereof.

3. The method defined in claim 1 wherein the compound of the formula I is apovincine or a pharmaceutically acceptable salt thereof.

4. The method defined in claim 1 wherein the dermatological composition is administered as a cream, ointment, solution, aerosol foam or injectable formulation suitable for subcutaneous or intracutaneous administration.

* * * * *

UNITED STATES PATENT AND TRADEMARK OFFICE
CERTIFICATE OF CORRECTION

PATENT NO. : 4,328,231  Page 1 of 2
DATED : 4 May 1982
INVENTOR(S) : Mária Zájer née Balázs et al It is certified that error appears in the above-identified patent and that said Letters Patent is hereby corrected as shown below:

Title Page
In the ABSTRACT, item [57], the formula should read as follows:

--
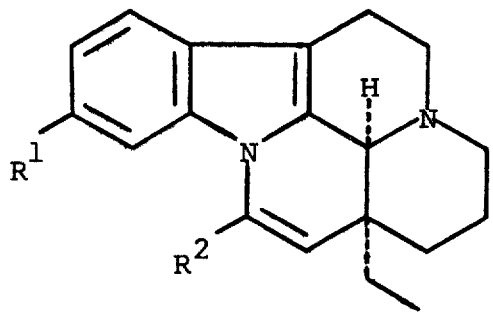
--.

UNITED STATES PATENT AND TRADEMARK OFFICE
CERTIFICATE OF CORRECTION

PATENT NO. : 4,328,231

DATED : 4 May 1982

INVENTOR(S) : Mária Zájer née Balázs et al

It is certified that error appears in the above-identified patent and that said Letters Patent is hereby corrected as shown below:

In column 8, claim 1, line 5, formula I should read as follows:

--

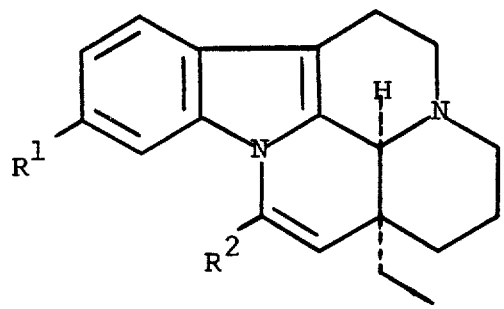

--.

Signed and Sealed this

Twenty-second Day of March 1983

[SEAL]

Attest:

GERALD J. MOSSINGHOFF

Attesting Officer

Commissioner of Patents and Trademarks